(12) United States Patent
Kassab et al.

(10) Patent No.: US 12,415,026 B2
(45) Date of Patent: *Sep. 16, 2025

(54) POINT OF INJURY DEVICE TO STABILIZE INTRACRANIAL PRESSURE AND METHOD OF STABILIZATION

(71) Applicant: 3DT Holdings, LLC, San Diego, CA (US)

(72) Inventors: Ghassan S. Kassab, La Jolla, CA (US); Ali Dabiri, San Diego, CA (US)

( * ) Notice: Subject to any disclaimer, the term of this patent is extended or adjusted under 35 U.S.C. 154(b) by 441 days.

This patent is subject to a terminal disclaimer.

(21) Appl. No.: 17/851,480

(22) Filed: Jun. 28, 2022

(65) Prior Publication Data

US 2022/0323664 A1    Oct. 13, 2022

Related U.S. Application Data (63) Continuation of application No. 16/211,031, filed on Dec. 5, 2018, now Pat. No. 11,369,721.

(60) Provisional application No. 62/594,923, filed on Dec. 5, 2017.

(51) Int. Cl.
| | |
|---|---|
| *A61M 1/00* | (2006.01) |
| *A61B 5/00* | (2006.01) |
| *A61B 5/03* | (2006.01) |
| *A61M 25/00* | (2006.01) |
| *A61M 27/00* | (2006.01) |
| *A61M 39/02* | (2006.01) |
| *A61M 25/01* | (2006.01) |

(52) U.S. Cl.
CPC ............. *A61M 1/772* (2021.05); *A61B 5/031* (2013.01); *A61B 5/036* (2013.01); *A61B 5/4836* (2013.01); *A61B 5/6852* (2013.01); *A61M 25/0029* (2013.01); *A61M 25/0075* (2013.01); *A61M 27/002* (2013.01); *A61M 39/0247* (2013.01); *A61M 2025/0166* (2013.01); *A61M 2027/004* (2013.01); *A61M 2039/0258* (2013.01); *A61M 2039/0273* (2013.01); *A61M 2039/0276* (2013.01); *A61M 2210/0693* (2013.01)

(58) Field of Classification Search
CPC .... A61M 1/772; A61M 1/77; A61M 25/0029; A61M 25/0075; A61M 27/002; A61M 39/0247; A61M 2025/0166; A61M 2027/004; A61M 2039/0258; A61M 2039/0273; A61M 2039/0276; A61M 2210/0693
See application file for complete search history.

(56) References Cited

U.S. PATENT DOCUMENTS

| | | | |
|---|---|---|---|
| 5,827,216 A * | 10/1998 | Igo | A61M 1/77 |
| | | | 604/176 |
| 11,369,721 B2 * | 6/2022 | Kassab | A61B 5/4836 |
| 2004/0147871 A1 * | 7/2004 | Burnett | A61M 39/24 |
| | | | 604/9 |

(Continued)

*Primary Examiner* — Philip R Wiest (57) ABSTRACT

A minimally invasive system for monitoring and treating high intracranial pressure levels resulting from traumatic brain injury comprises an intravenous access device, an elongate member, a console, and an aspiration and injection catheter. The system is capable of monitoring pressure levels and relocating fluid from the brain to another part of the patient's body to sustain overall constant fluid volume. The method of using the minimally invasive system is also described.

16 Claims, 6 Drawing Sheets

(56) References Cited

U.S. PATENT DOCUMENTS

2010/0022950 A1\* 1/2010 Anderson .......... A61B 1/00114
604/100.01
2017/0333687 A1\* 11/2017 Murphy ................ A61M 27/00
2018/0056050 A1\* 3/2018 Degen ................. A61M 27/002

\* cited by examiner

POINT OF INJURY DEVICE TO STABILIZE INTRACRANIAL PRESSURE AND METHOD OF STABILIZATION

PRIORITY

The present application is related to, and claims the priority benefit of, and is a U.S. continuation patent application of U.S. patent application Ser. No. 16/211,031, filed Dec. 5, 2018, and issued as U.S. Pat. No. 11,369,721 on Jun. 28, 2022, which is related to, and claims the priority benefit of U.S. Provisional Patent Application Ser. No. 62/594,923, filed Dec. 5, 2017, the contents of which are incorporated herein directly and by reference in their entirety.

BACKGROUND

Each year, traumatic brain injuries (TBIs) contribute to a substantial number of deaths and cases of permanent disability. In fact, TBI is a contributing factor to a third (30%) of all injury-related deaths in the United States. In 2010, approximately 2.5 million people sustained a TBI. Individuals with more severe injuries are more likely to require hospitalization.

A severe TBI not only impacts the life of an individual and their family, but it also has a large societal and economic toll. The estimated economic cost of TBI in 2010, including direct and indirect medical costs, is estimated to be approximately $76.5 billion. Additionally, the cost of fatal TBIs and TBIs requiring hospitalization, many of which are severe, account for approximately 90% of the total TBI medical costs.

Neurological damage from TBI is a consequence of both the moment of impact or injury (primary injury) as well as the secondary injury that evolves over the subsequent hours and days post-injury. To maximize outcomes, TBI care should begin as soon as possible after injury to mitigate the secondary, delayed insults. Ideally, such care should be performed within the "golden hour." Early resuscitative attempts may include hemorrhage control, hypertonic saline, prehospital endotracheal intubation and hyperventilation. The overall goal of medical and surgical treatment for severe TBI is to prevent secondary injury by maintaining blood flow and oxygen delivery to the brain while minimizing swelling and pressure overload.

The degree of secondary injury has a critical impact on outcome, and early detection of these secondary events is a major target of neuromonitoring. The most widely accepted neuromonitoring parameters, intracranial pressure, cerebral perfusion and seizure activity, have been shown to be related to mortality after traumatic brain injury in many studies. Consequently, medical and surgical efforts attempt to normalize intracranial pressure to maintain cerebral blood flow and prevent death.

Neurocritical care must focus on treating the secondary injury to stabilize the patient to prevent further brain injury. Concerns of delayed non-mechanical damage include swelling of the brain, inadequate oxygenation and metabolic dysfunction. The swelling of the brain is accompanied by an increase in intracranial pressure which prevents the cerebrospinal fluid from draining out of the skull. If this is not prevented or controlled, the brain can herniate (push through) the base of the skull and cause respiratory failure and possibly death.

Factors Affecting Increased Intracranial Pressure

According to the Monro-Kellie doctrine, the incompressible skull, blood, cerebrospinal fluid and brain tissue exist in a state of volume equilibrium, such that any increase in volume of one of the cranial constituents must be compensated by a decrease in volume of another.

The cerebrospinal fluid is contained in the brain ventricles and the cranial and spinal subarachnoid spaces. The mean cerebrospinal fluid volume is 150 ml, with 25 ml in the ventricles and 125 ml in subarachnoid spaces. Cerebrospinal fluid is predominantly, but not exclusively, secreted by the choroid plexuses. Brain interstitial fluid, ependyma and capillaries may also play a poorly defined role in cerebrospinal fluid secretion. Cerebrospinal fluid circulation from sites of secretion to sites of absorption largely depends on the arterial pulse wave. Additional factors such as respiratory waves, posture, jugular venous pressure and physical effort also modulate cerebrospinal fluid flow dynamics and pressure.

Cranial and spinal arachnoid villi have been considered for a long time to be the predominant sites of cerebrospinal fluid absorption into the venous outflow system. Experimental data suggest that cranial and spinal nerve sheaths, the cribriform plate and the adventitia of cerebral arteries constitute substantial pathways of cerebrospinal fluid drainage into the lymphatic outflow system, but these pathways play only a minor role.

The initial compensatory mechanism for intracranial volume expansion following TBI or ischemic edema, for example, would be a reduction in cerebrospinal fluid. Once all compensatory mechanisms have been exhausted, intracranial pressure rapidly rises resulting in decreased cerebral perfusion pressure as demonstrated by the formula CPP=MAP−ICP (where MAP denotes mean arterial pressure). In the absence of autoregulation, cerebral perfusion pressure determines cerebral blood flow and, therefore, oxygen supply. Intracranial pressure must be measured directly as it cannot otherwise be estimated by any clinical feature or imaging (e.g. computed tomography, CT). Normal intracranial pressure depends on age and body position, and ranges from 7 to 15 mmHg in healthy adults. Above 20-25 mmHg, aggressive treatment is started in most intensive care units. Lower thresholds have been suggested for children.

It was believed that the intracranial pressure level would be determined by the rates of cerebrospinal fluid formation and absorption, but there is at least one other parameter that contributes to the level of pressure which is called the vascular contribution. One study observed the relative contribution of cerebrospinal fluid and vascular parameters to the level of intracranial pressure in 34 severely head-injured patients. The cerebrospinal fluid parameters involve the cerebrospinal fluid formation, F, and cerebrospinal fluid absorption. The cerebrospinal fluid formation averaged 0.337 ml/min with standard deviation of 0.1 ml/min in patients with head injury and intracranial pressure levels <15 mmHg. As intracranial pressure levels increased to >25 mmHg, the mean rate of cerebrospinal fluid formation dropped moderately to 0.296 with a standard deviation of 0.06 ml/min. Although this range is still within the normal range of cerebrospinal fluid formation, it indicates that the cerebrospinal fluid formation decreases as intracranial pressure increases. The cerebrospinal fluid formation also remained within the normal range during the 5-day post-injury period with a tendency to drop over time. The cerebrospinal fluid absorption is represented by the resistance to outflow, R, which is about 3.0 mmHg/ml/min in normal conditions. Therefore, normal contribution of cerebrospinal fluid to pressure is F×R=1.0 mmHg. The normal vascular contribution of intracranial pressure, $P_{vnorm}$, can be estimated by inserting the normal values for cerebrospinal fluid formation, F, outflow resistance, R, and intracranial pressure, ICP, in the steady state equation:

$$ICP = F \times R \times P_{vnorm} \quad (1)$$

In this scenario, the $P_{vnorm}$ is about 1 mmHg less than the intracranial pressure.

The study also performed bolus injections to increase intracranial pressure to about 35 mmHg to observe the variation of cerebrospinal fluid formation and absorption to simulate hemorrhage. As noted above, the cerebrospinal fluid formation did not change significantly with increase of intracranial pressure. The resistance to cerebrospinal fluid absorption increased substantially, however, with a mean of 7 mmHg/ml/min. The increase was higher in the case of intracranial pressure's higher than 15 mmHg and the maximum can reach up to 20 mmHg/ml/min. This increase was sustained and did not change significantly during the 5-day observation period.

The percent contributions of cerebrospinal fluid and vascular components were calculated in connection with the present disclosure. The mean steady state intracranial pressures in the group of 19 patients were 16.8 mmHg. It was found that the component of intracranial pressure rise due to cerebrospinal fluid absorption accounted for an average of 33% of the intracranial pressure elevation while the remainder was due to the vascular contribution. The vascular contribution was even more predominant in patients with intracranial pressure greater than 20 mmHg.

The fact that the high levels of outflow resistance are associated with intracranial hemorrhage have also been reported by several investigators. One studied cerebrospinal fluid dynamics in patients with intracranial hemorrhage and found linear correlation between outflow resistance and steady-state intracranial pressure. He found that nearly 90% can be attributed to the increase in outflow resistance. Another found that outflow resistance to be elevated in patients by threefold in cases with subarachnoid hemorrhage.

It is therefore important to note that the equation (1) is not applicable to head-injured patients and needs to be modified to include a volume-induced rise in intracranial pressure which is not subject to cerebrospinal fluid flow hydrodynamics. The resulting intracranial pressure increase acts primarily to compress the more compliant vessels. Intravascular pressure on the venous side of the circulation increases as a result of this compression and is reflected by the high vascular component measured. A study found that a decrease in arterial blood pressure from 100 to 51 mmHg caused a 25% decrease in cerebrospinal fluid outflow resistance in New Zealand White rabbits.

One can conclude that there is evidence that the intracranial pressure can be decreased by intentionally reducing nearby venous or arterial pressure.

Intracranial Pressure Monitoring and Stabilization

Intracranial pressure monitoring is the most widely used technical neuromonitoring device. Currently, a catheter placed into one of the lateral ventricles and connected to an external pressure gauge is the most reliable and low-cost method for intracranial pressure monitoring. This is the most frequently used method as it measures global intracranial pressure, provided there is no obstruction of cerebrospinal fluid flow. It also allows therapeutic drainage of cerebrospinal fluid to reduce intracranial pressure, and can be recalibrated in situ.

Ventricular catheters are associated with a higher infection risk, however, as compared to intraparenchymal catheters. These catheters can be difficult to place into brains with severe swelling. Intraparenchymal catheters are easier to place, and infections are rare. This approach uses a fiber-optic transducer or a piezo element on the tip of the catheter. Accuracy is usually good and although recalibration is not possible, baseline drift is low.

It is possible that the pressure measured by the probe, however, does not represent global intracranial pressure. The theoretical concept of an intracranial space as a single chamber with an equal distribution of pressure is not always correct, as intracranial pressure in TBI patients for example may be unequally distributed throughout the cranial vault. The risk of developing an intracranial pressure gradient may depend on the cause of damage. Focal lesions have been shown to cause an interhemispheric pressure shift, while in diffuse lesions no interhemispheric difference was shown. Intraparenchymal probes should preferably be placed at the side of a mass lesion to avoid overestimation of cerebral perfusion pressure. An important disadvantage of intraparenchymal probes is the higher cost as well as the lack of ability for cerebrospinal fluid drainage.

Monitoring of intracranial pressure and cerebral perfusion pressure remains a cornerstone in severe brain injury, particularly if a brain CT scan is abnormal despite the lack of primary evidence. It is important, however, not to rely on these two components alone. Aside from intracranial pressure and cerebral perfusion pressure, it is important to apply a multimodal therapeutic approach for the optimization of cerebral blood flow, oxygen delivery and brain energy supply and early detection of clinically hidden epileptic seizures by EEG to improve overall care of brain injured patients. There is clinical evidence that demonstrates that multimodal brain monitoring may help optimize cerebral blood flow and the delivery of oxygen/energy substrate at bedside, thereby improving the management of secondary brain injury.

Thus, there is much room for needed improvement in the space of TBI treatment and intracranial pressure monitoring. Ideally, such a treatment would be minimally invasive, simple to use and the process would be quick to perform and ideally within the "golden hour." In addition, the process would be accurate and easily repeatable.

BRIEF SUMMARY

The present disclosure includes disclosure of systems and devices to stabilize intracranial pressure, as described and/or shown herein.

The present disclosure includes disclosure of systems to stabilize intracranial pressure, comprising one or more intravenous access devices; and/or one or more elongate members; and/or one or more consoles; and/or one or more aspiration and injection catheters.

The present disclosure includes disclosure of a system to stabilize intracranial pressure, comprising an intravenous access device, an elongate member, and an aspiration and injection catheter having a first end, a second end, and a third end, the aspiration and injection catheter configured so that the first end and the second end can be positioned at least partially within a mammalian body, and further configured so that the third end can operably connect to a suction or injection device.

In at least one embodiment, the first end, the second end, and the third end are in fluid communication with each other.

In at least one embodiment, the system further comprises one or more valves positioned within the aspiration and injection catheter, the one or more valves designed to direct flow from at least one of the first end, the second end, or the third end, to another of the first end, the second end, or the third end.

In at least one embodiment, the system further comprises a first valve and a second valve positioned within the aspiration and injection catheter, each of the first valve and the second valve comprising an open and a closed position.

In at least one embodiment, when the first valve is open and the second valve is closed, fluid within the aspiration and injection catheter may travel from the first end to the third end.

In at least one embodiment, when the first valve is closed and the second valve is open, fluid within the aspiration and injection catheter may travel from the third end to the second end.

In at least one embodiment, the aspiration and injection catheter further comprises a pressure monitor configured to obtain pressure data within the aspiration and injection catheter.

In at least one embodiment, the aspiration and injection catheter is configured to connect to the intravenous access device.

In at least one embodiment, the aspiration and injection catheter is in fluid communication with the intravenous access device.

In at least one embodiment, the system further comprises a console in communication with the elongate member and configured to obtain data from an electrode section of the elongate member.

The present disclosure includes disclosure of a method to stabilize intracranial pressure of a patient, comprising the steps of placing a first end of an aspiration and injection catheter into a target site of a brain of a patient, placing a second end of the aspiration and injection catheter at a location in a vasculature of the patient and outside of a venous sinus of the brain of the patient, and placing a third end of the aspiration and injection catheter exterior to the patient, wherein the aspiration and injection catheter is configured to facilitate a flow of blood and from the brain of the patient, though the aspiration and injection catheter, and into to the vasculature of the patient.

In at least one embodiment, the method further comprises the steps of monitoring intracranial pressure of the patient, and aspirating blood from the brain of the patient when the intracranial pressure is at or above a threshold limit.

In at least one embodiment, the target site is the venous sinus of the brain of the patient, and wherein the step of aspirating blood is performed to aspirate blood from the venous sinus of the brain of the patient.

In at least one embodiment, the step of aspirating the blood from the venous sinus of the brain is performed to aspirate the blood into the first end of the aspiration and injection catheter and out of the third end of the aspiration and injection catheter.

In at least one embodiment, the step of aspirating blood is performed by operating a suction or injection device connected to the third end of the aspiration and injection catheter.

The present disclosure includes disclosure of a method to stabilize intracranial pressure of a patient, comprising the steps of advancing an elongate member of a system to a target site of a brain of a patient, the system comprising an intravenous access device, the elongate member, and an aspiration and injection catheter having a first end, a second end, and a third end, the aspiration and injection catheter configured so that the first end and the second end can be positioned at least partially within a mammalian body, and further configured so that the third end can operably connect to a suction or injection device; advancing at least part of the intravenous access device over at least part of the elongate member; and advancing the aspiration and injection catheter through the intravenous access device such that the first end is at the target site sinus of the brain of the patient, the second end is at a location in the vasculature of the patient and outside the venous sinus, and the third end is exterior of the patient.

In at least one embodiment, the elongate member is introduced into the patient via an access site on the patient.

In at least one embodiment, the access site is selected from the group consisting of a radial vein, a cephalic vein, a brachial vein, a basilica vein, and a saphenous vein, in an arm of the patient.

In at least one embodiment, the elongate member is a conductance guidewire in communication with the console connected thereto, and wherein the step of advancing the elongated member is performed while obtaining conductance information, the conductance information processed by the console and displayed on the console to facilitate advancement of the conductance guidewire.

In at least one embodiment, the intravenous access device is selected from the group consisting of an indwelling catheter, a peripherally inserted central catheter, and a central venous catheter.

The present disclosure includes an exemplary system to stabilize intracranial pressure of the present disclosure comprising an intravenous access device, an elongate member, a console, and an aspiration and injection catheter.

In at least one embodiment, the aspiration and injection catheter comprises a first end, a second end and a third end.

In at least one embodiment, wherein the first end, the second end and the third end are in fluid communication with each other.

In at least one embodiment, an exemplary system also comprises a valve or a series of valves designed to direct flow from one catheter end to another catheter end.

In at least one embodiment, the system comprises a first valve and a second valve positioned on the aspiration and injection catheter, each valve comprising an open and a closed position.

In at least one embodiment, when the first valve is open and the second valve is closed, fluid may travel from the first end to the third end.

In at least one embodiment, when the first valve is closed and the second valve is opened, fluid may travel from the third end to the second end.

In at least one embodiment, the aspiration and injection catheter comprises a pressure monitor.

In at least one embodiment, the aspiration and injection catheter is configured to connect to the intravenous access device.

In at least one embodiment, the aspiration and injection catheter is in fluid communication with the intravenous access device.

The present disclosure includes disclosure of methods to stabilize intracranial pressure, using one or more devices and/or systems of the present disclosure, as described and/or shown herein.

The present disclosure includes an exemplary method to stabilize intracranial pressure of a patient using an exemplary device of the present disclosure comprising the steps of: deploying an aspiration and injection catheter comprising a first end, a second end and a third end in the patient; wherein deploying the aspiration and injection catheter comprises the steps of: placing the first end in a target site of the brain of the patient; placing the second end at a location in the vasculature of the patient and outside the venous sinus; and placing the third end exterior to the patient.

In at least one embodiment, an exemplary method to stabilize intracranial pressure of a patient further comprises the steps of: monitoring the intracranial pressure; and aspirating blood from the target site of the brain when the intracranial pressure is too high.

In at least one embodiment, an exemplary method to stabilize intracranial pressure of a patient comprises a target site is of the venous sinus of the brain.

In at least one embodiment, an exemplary method to stabilize intracranial pressure of a patient further comprises the step of aspirating the blood into the first end and out of the third end.

In at least one embodiment, an exemplary method to stabilize intracranial pressure of a patient further comprises the step of reintroducing the aspirated blood into the vasculature of the patient via the second end.

In at least one embodiment, an exemplary method to stabilize intracranial pressure of a patient using an exemplary device of the present disclosure comprises the steps of: deploying the exemplary device in the patient wherein the exemplary device comprises: an intravenous access device, an elongate member, a console, an aspiration and injection catheter comprising a first end, a second end and a third end; and deploying the device comprises the steps of: advancing the elongate member to the target site in the brain; advancing the intravenous access device over the elongate member; and advancing the aspiration and injection catheter through the intravenous access device such that the first end is at the target site sinus of the brain of the patient, the second end is at a location in the vasculature of the patient and outside the venous sinus and the third end is exterior of the patient.

In at least one embodiment, an exemplary method to stabilize intracranial pressure of a patient comprises the step of introducing the elongate member into the patient via an access site on the patient.

In at least one embodiment, an exemplary method to stabilize intracranial pressure of a patient comprises an access site comprising a radial, a cephalic, a brachial, a basilica or a saphenous vein in an arm of the patient.

In at least one embodiment, an exemplary method to stabilize intracranial pressure of a patient comprises an elongate member comprising a conductance guidewire in communication with the console and the information displayed on the console directs the advancement of the conductance guidewire.

In at least one embodiment, an exemplary method to stabilize intracranial pressure of a patient comprises an intravenous access device comprising an indwelling catheter, a peripherally inserted central catheter or a central venous catheter.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. For example, the system is referred to as being used to treat traumatic brain injury, but can be used to monitor and treat increases in intracranial pressure generally. Even further the device could be further applicable to reduce vessel pressure generally.

As described above, the intracranial pressure level can be determined by the rates of cerebrospinal fluid formation and absorption. This is not true in case of head-injured patients with hemorrhage where there is volume-induced rise in intracranial pressure which is not subject to cerebrospinal fluid flow hydrodynamics. There is at least one additional parameter that contributes to the level of intracranial pressure, called the vascular contribution.

The present disclosure provides for a system and method of monitoring and stabilizing the intracranial pressure of an injured patient by monitoring and altering the vascular contribution.

Exemplary System Elements

Figure 1:
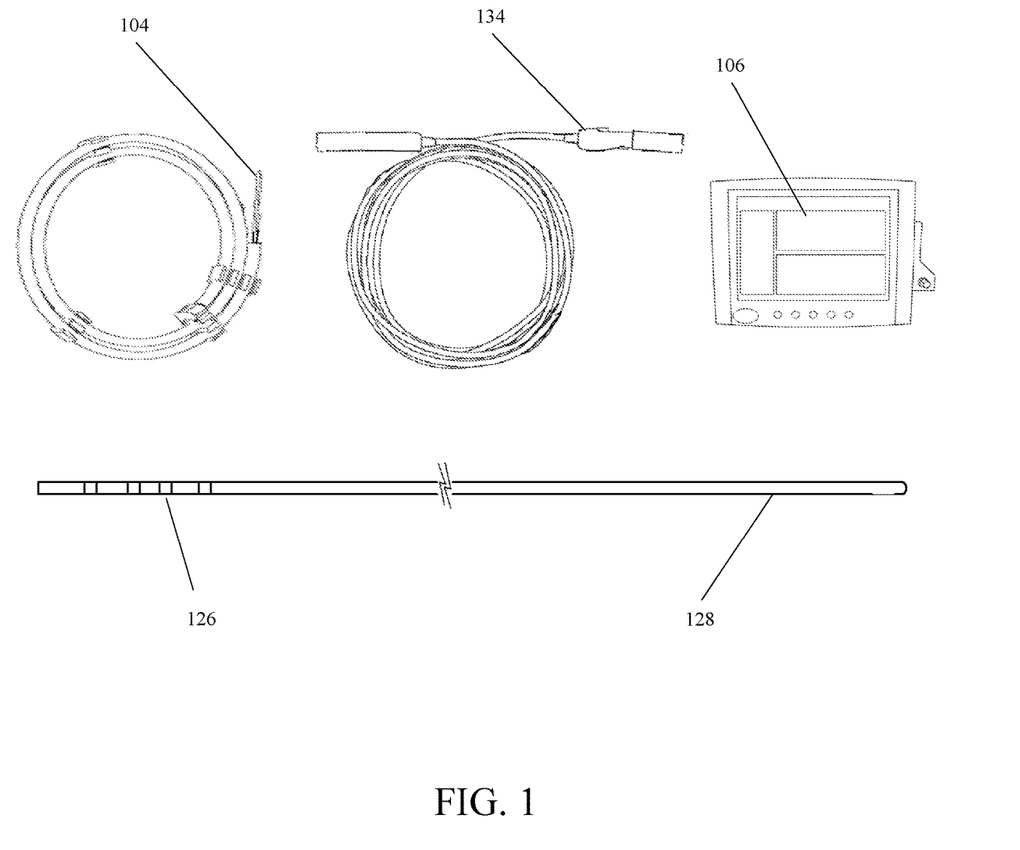
FIG. 1 shows a guidewire system for navigating to a target site in the brain, according to an exemplary embodiment of the present disclosure.
Figure 4:
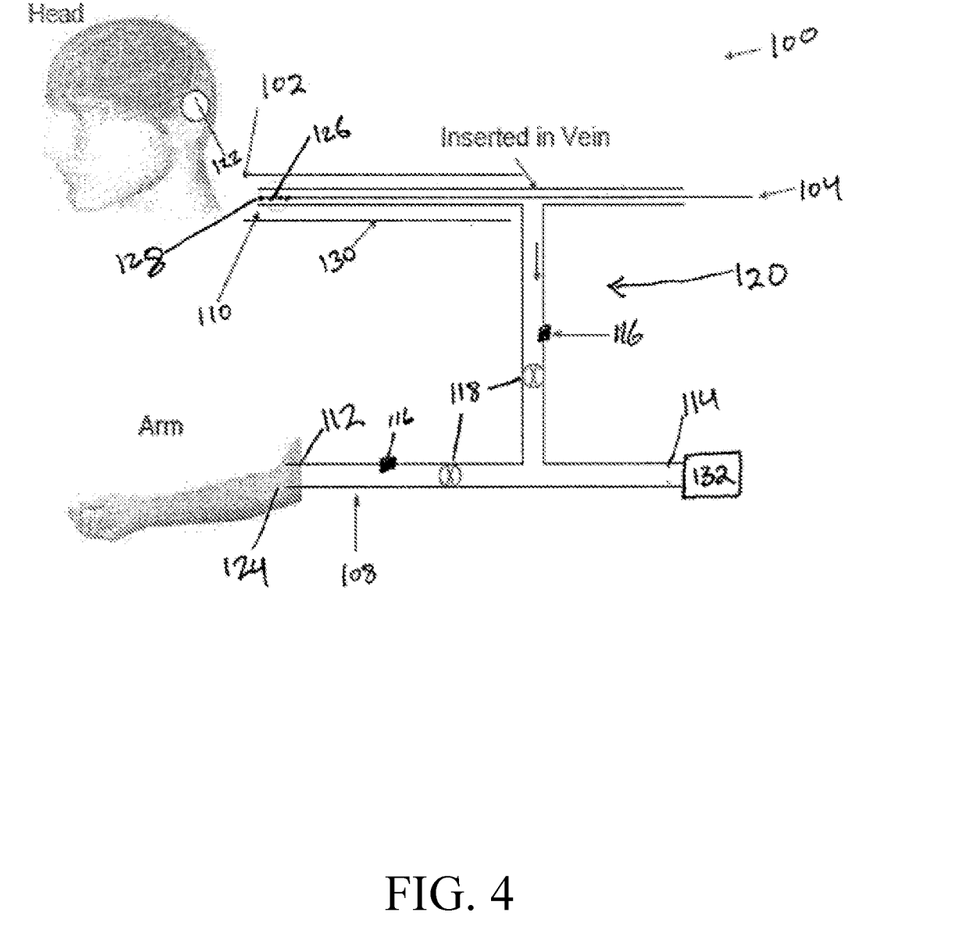
FIG. 4 shows a visual schematic of the device, according to an exemplary embodiment of the present disclosure.
Figure 5:
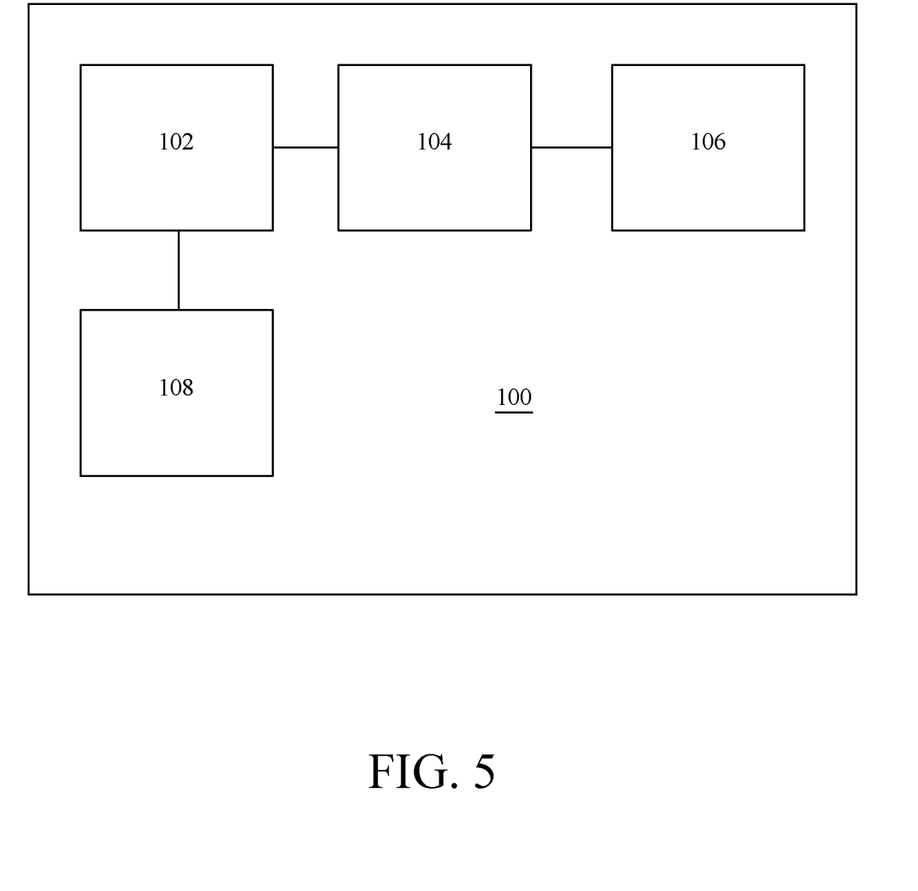
FIG. 5 shows a block diagram representation of the device, according to an exemplary embodiment of the present disclosure.

In one embodiment of the present disclosure, an exemplary system 100 comprises an intravenous access device 102, an elongate member 104, a console 106, and an aspiration and injection catheter 108, such as shown in FIGS. 1, 4, and 5 and referenced in further detail herein.

The intravenous access device 102 is used to obtain access to the patient's bodily lumens, usually the blood vessels 130, from the exterior of the patient. The intravenous access device 102 should be of a diameter such that it can be intraluminally advanced over a guidewire from the access site 124 to the desired target site 122, such as the venous sinuses. The intravenous access device 102 may be an indwelling catheter, and in at least one exemplary one embodiment, the intravenous access device 102 is a peripherally inserted central catheter (PICC), or in another exemplary embodiment, a central venous catheter (CVC).

Similarly, the elongate member 104 may be a guidewire capable of navigating to the venous sinuses or other target site 122. As shown in FIG. 1, the guidewire (an exemplary elongate member 104) may comprise a handle 134 connected to a body, such as long-coiled body around a solid core. The long-coiled body may comprise a floppy or atraumatic distal tip 128 and a stiff proximal end for easy manipulation that is connected to the handle 134. The elongate member 104 may be a conductance guidewire comprising a tetrapolar electrode section 126 for measurement, such as disclosed within U.S. Pat. No. 7,454,244, issued on Nov. 18, 2008 to Kassab et al., the contents of which are hereby incorporated into the present disclosure directly and by reference. The electrode section 126, which can include one, two, three, four, or more electrodes in various embodiments, is preferably located near the distal end of the guidewire and proximal of the atraumatic tip 128. The electrode section 126 may comprise any appropriate number of electrodes 126, and there may be more than one electrode section 126 on the guidewire.

Figure 2:
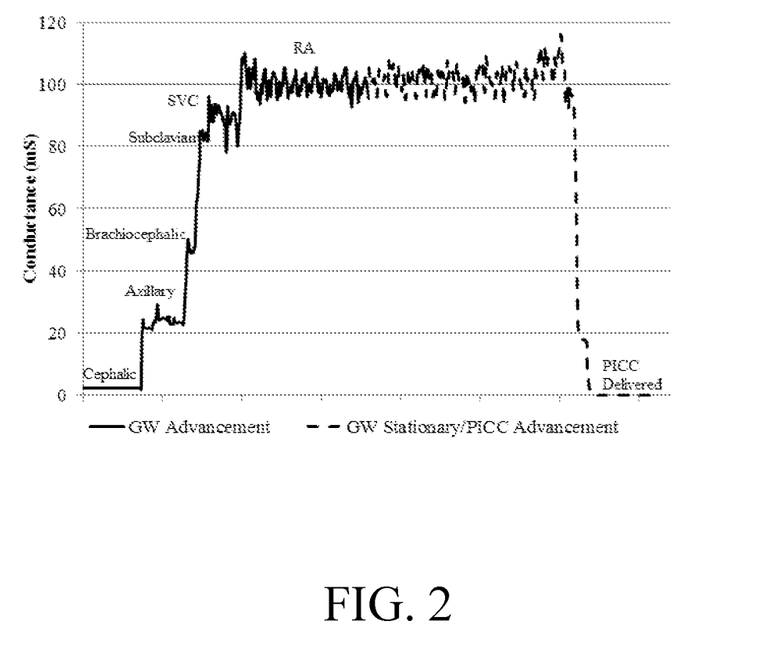
FIG. 2 shows an exemplary conductance chart of guidewire navigation to the right atrium, according to an exemplary embodiment of the present disclosure.
Figure 3A:
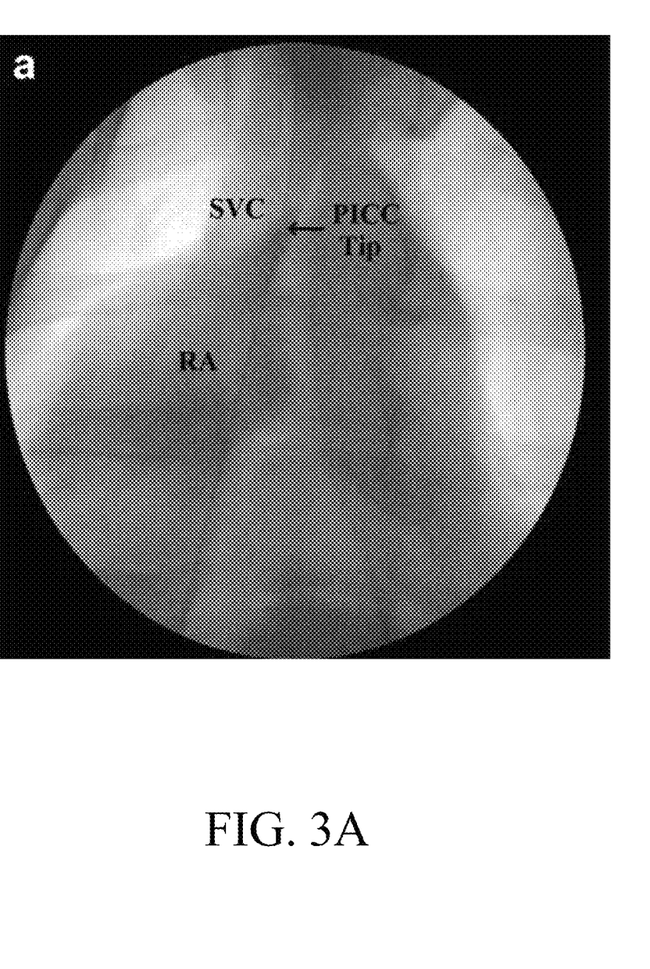
FIG. 3A shows a fluoroscopic visualization of the present device deployed at a target site, according to an exemplary embodiment of the present disclosure.
Figure 3B:
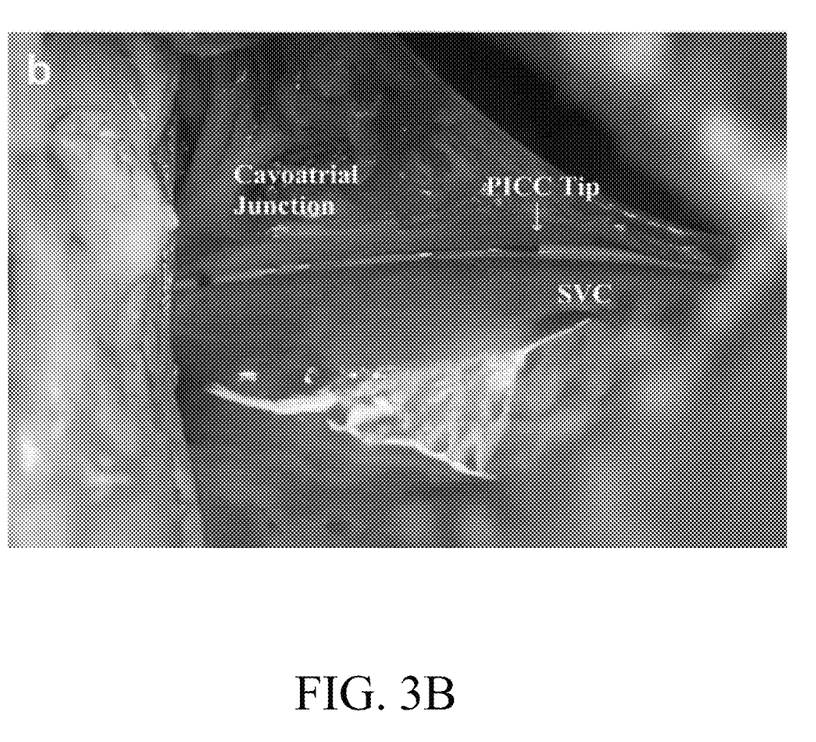
FIG. 3B shows a direct visual of the present device deployed at a target site, according to an exemplary embodiment of the present disclosure.

An exemplary console 106 is shown in FIG. 1. The console 106 is in communication with the conductance guidewire and receives conductance information from the guidewire. The console 106 may comprise a computer or processor that interprets the information and displays the interpreted information on a screen display for viewing by the clinician. In a preferred embodiment, the screen display shows increased conductance and oscillations during guidewire advancement in the correct direction towards out target junction, but sustained decreased conductance during guidewire advancement in the incorrect direction away from the junction as in FIG. 2. The clinician can then use the increasing or decreasing oscillations and conductance to accurately navigate the guidewire to a target site 122.

The aspiration and injection catheter 108 is connected to and in fluid communication with the intravenous access device 102. The aspiration and injection catheter 108 may comprise a single catheter, or multiple catheters connected so as to share lumens. The catheter may have a valve or series of valves 118 designed to direct fluid flow from one catheter end to another catheter end. The valve or valves 118 may be open or closed as desired to aspirate or to inject fluid. The aspiration and injection catheter 108 may also have pressure monitors 116 to detect the fluid pressure (pressure data/information) within the connected lumens. The pressure monitors are preferably installed upstream of each valve.

An exemplary aspiration and injection catheter 108 is also shown in FIG. 4. As shown in FIG. 4, the intravenous access device 102 has been introduced over a guidewire into the patient at one of the radial veins and advanced to the venous sinuses of the patient. The aspiration and injection catheter 108 is capable of being placed over the guidewire and connected with the intravenous access device 102.

In the exemplary embodiment depicted in FIG. 4, the aspiration and injection catheter 108 has a first end 110 disposed so as to accept fluid, as in blood, from the venous sinuses. A second end 112 is disposed so as to accept blood from a radial vein in the arm of the patient. A third end 114 is exterior to the patient and accessible to the clinician. The three ends are in fluid communication with each other via a shared lumen junction.

As depicted in FIG. 4, a first valve is placed upstream of the lumen junction 120 towards the first end 110 so that it prevents fluid flow in and out of the first end 110 when closed. A second valve is placed toward the second end 112 and upstream of the lumen junction 120 so that when closed, it prevents fluid flow into or out of the second end 112. The valves 118 are placed upstream so that when the first valve is closed and the second valve opened, fluid may be introduced into the third end 114 and forced to exit the second end 112 into the radial vein, and when the first valve is opened and the second valve is closed, fluid from the first end 110 may be removed via the third end 114 by application of a suctioning force (via a suction or injection device 132) at the third end 114. The introduction and suctioning of fluid may be provided by a syringe (an exemplary suction or injection device 132).

For further clarification, FIG. 5 a block diagram of the system components may be referred to. As shown in FIG. 5, the elongate member 104 and the aspiration and injection catheter 108 interact with the intravenous access device 102, while the elongate member 104 is in communication with the console 106. The four components comprise the system for treating traumatic brain injury 100.

Exemplary Procedure

An exemplary method of using the system to treat secondary traumatic brain injury (e.g. increase in intracranial pressure) comprises the steps of introducing and navigating a guidewire to the a target site 122 in the brain, deploying the intravenous access device 102, deploying the aspiration and injection catheter 108 and monitoring and reducing intracranial pressure as necessary.

Preferably a minimally invasive method such as micropuncture surgery is used to introduce the elongate member 104 or guidewire. Preferred access sites 124 include the radial, cephalic, brachial, basilica, or saphenous veins in the arm of the patient. Other extremities or veins may be used as appropriate or medically necessary. The tip of the guidewire is then advanced to a target site 122, preferably the veins of the brain. Preferably, a conductance guidewire, like the one described above, is used so that navigation is aided by measuring and comparing the parallel conductances of the bodily vessels. Conductance readings can be sent to the console 106 and displayed in real time on an associated screen display. Tip location can be accurately and readily assessed by the clinician and navigation decisions can be made in real time, thereby reducing deployment time.

An exemplary pathway for the elongate member 104 could include initial entry at an access site 124 in the cephalic vein then proceeding into the axillary, brachiocephalic, subclavian superior vena cava and ending in the right atrium. In this exemplary method, each subsequent vein is larger in diameter than the previous. Thus, the measured conductance will show step increases as the guidewire reaches each new, larger vessel, while navigation away from the larger vessels will result in decreases in conductance. A clinician can use these increases and decreases to determine if the guidewire is moving toward or away from a target site 122 in the brain. The point at which there is the largest absolute conductance coupled with large pulsatile conductance changes denotes the location of the cavoatrial junction.

Once the tip of the guidewire has reached the target site 122, the guidewire can be held in place and the intravenous access device 102 can be advanced over the guidewire. If an exemplary guidewire having an electrode section 126 at its distal tip is used, once the intravenous access device 102 covers the electrode section 126, the displayed conductance will drop abruptly to almost zero, signaling to the clinician that the intravenous access device 102 is in place. Where a peripherally inserted central catheter or a central venous catheter has been used, it can be taped to the patient to secure the device.

At this point the aspiration and injection catheter 108 can be connected to or placed into the intravenous access device 102. The associated pressure monitors 116 can be used to observe intracranial pressure. When intracranial pressure gets too high, the appropriate valves 118 may be closed and blood aspirated from the venous of the brain, thereby lowering the cerebrospinal fluid. This blood can be reintroduced into the patient's body by closing the appropriate valves 118 and injecting the blood into the guidewire introduction site which in the exemplary embodiment is the cephalic vein.

The method can be summarized as comprising the steps of accessing the target site 122 via a elongate member 104 introduced into a patient at an access site 124, advancing the guidewire through the vasculature to the target site 122, advancing the intravenous access device 102 to the target site 122 over the guidewire, attaching the aspiration and injection catheter 108 to the intravenous access device 102, taking a pressure measurement, treating the patient by aspirating blood through the intravenous access device 102 and aspiration and injection catheter 108 and reintroducing the blood through the aspiration and injection catheter 108 at the access site 124.

While various embodiments of devices for a point of injury device for monitoring and stabilizing intracranial pressure and methods for treating traumatic brain injury using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system to stabilize intracranial pressure, comprising:
   an intravenous access device;
   an elongate member comprising at least one electrode section, the at least one electrode section having at least one electrode thereon; and
   an aspiration and injection catheter having a first end, a second end, and a third end, the aspiration and injection catheter configured so that the first end and the second end can be positioned at least partially within a mammalian body, and further configured so that the third end can operably connect to a suction or injection device.

2. The system of claim 1, wherein the first end, the second end, and the third end are in fluid communication with each other.

3. The system of claim 1, further comprising:
   one or more valves positioned within the aspiration and injection catheter, the one or more valves designed to direct flow from at least one of the first end, the second end, or the third end, to another of the first end, the second end, or the third end.

4. The system of claim 1, further comprising:
   a first valve and a second valve positioned within the aspiration and injection catheter, each of the first valve and the second valve comprising an open and a closed position.

5. The system of claim 4, wherein when the first valve is open and the second valve is closed, fluid within the aspiration and injection catheter may travel from the first end to the third end.

6. The system of claim 4, wherein when the first valve is closed and the second valve is open, fluid within the aspiration and injection catheter may travel from the third end to the second end.

7. The system of claim 1, wherein the aspiration and injection catheter further comprises a pressure monitor configured to obtain pressure data within the aspiration and injection catheter.

8. The system of claim 1, wherein the aspiration and injection catheter is configured to connect to the intravenous access device.

9. The system of claim 8, wherein the aspiration and injection catheter is in fluid communication with the intravenous access device.

10. The system of claim 1, further comprising:
    a console in communication with the elongate member and configured to obtain data from the at least one electrode section of the elongate member.

11. A method to stabilize intracranial pressure of a patient, comprising the steps of:
    advancing an elongate member of a system to a target site of a brain of a patient, the system comprising:
       an intravenous access device,
       the elongate member, wherein the elongate member comprises at least one electrode section, the at least one electrode section having at least one electrode thereon, and
       an aspiration and injection catheter having a first end, a second end, and a third end, the aspiration and injection catheter configured so that the first end and the second end can be positioned at least partially within a mammalian body, and further configured so that the third end can operably connect to a suction or injection device;
    advancing at least part of the intravenous access device over at least part of the elongate member; and
    advancing the aspiration and injection catheter through the intravenous access device such that the first end is at the target site sinus of the brain of the patient, the second end is at a location in the vasculature of the patient and outside the venous sinus, and the third end is exterior of the patient.

12. The method of claim 11, wherein the elongate member is introduced into the patient via an access site on the patient.

13. The method of claim 12, wherein the access site is selected from the group consisting of a radial vein, a cephalic vein, a brachial vein, a basilica vein, and a saphenous vein, in an arm of the patient.

14. The method of claim 11, wherein the elongate member is a conductance guidewire in communication with a console connected thereto, and wherein the step of advancing the elongated member is performed while obtaining conductance information from the at least one electrode section.

15. The method of claim 14, wherein the conductance information is processed by the console and displayed on the console to facilitate advancement of the conductance guidewire.

16. The method of claim 11, wherein the intravenous access device is selected from the group consisting of an indwelling catheter, a peripherally inserted central catheter, and a central venous catheter.

\* \* \* \* \*